United States Patent [19]

Lindmayer

[11] Patent Number: 4,662,878
[45] Date of Patent: May 5, 1987

[54] MEDICINE VIAL ADAPTOR FOR NEEDLELESS INJECTOR

[75] Inventor: Istvan Lindmayer, Pierrefonds, Canada

[73] Assignee: Patents Unlimited Ltd., Hamilton, Bermuda

[21] Appl. No.: 797,529

[22] Filed: Nov. 13, 1985

[51] Int. Cl.⁴ .............................................. A61M 5/30
[52] U.S. Cl. ....................................... 604/411; 604/71
[58] Field of Search .................................. 604/68–72, 604/90, 405, 407, 411, 414

[56] References Cited

U.S. PATENT DOCUMENTS

| | | | |
|---|---|---|---|
| 3,292,622 | 12/1966 | Banker | 128/173 |
| 3,526,225 | 9/1970 | Isobe | 128/173 |
| 4,507,113 | 3/1985 | Dunlap | 604/411 |
| 4,518,385 | 5/1985 | Lindmayer et al. | 604/68 |
| 4,564,054 | 1/1986 | Gustavsson | 604/411 |
| 4,568,336 | 2/1986 | Cooper | 604/905 |

Primary Examiner—C. Fred Rosenbaum
Assistant Examiner—Sherri E. Vinyard
Attorney, Agent, or Firm—Wegner & Bretschneider

[57] ABSTRACT

A disposable plastic adaptor connects a medicine vial to a needleless injector. It includes a hollow, generally cylindrical body member having a top end and a bottom end, with a wall dividing said hollow body into a generally cylindrical top end cavity and bottom end cavity. The bottom end cavity is adapted to slide over the top end of a medicine vial and the cavity wall includes a plurality of detents which prevent removal of the adaptor from the vial. The top end cavity is adapted to be twist connected to the end of a needleless injector. A fluid connector member is mounted within the body member and it comprises a sharp tipped probe extending axially downwardly within the bottom end cavity and an axial projection with a concave end face extending axially upwardly within the top end cavity. An axial bore extends through the fluid connector member to flow connect the concave end face and the probe tip. This probe, preferably in the form of a hollow needle, is adapted to penetrate the top of a medicine vial and the concave end face is adapted to provide a fluid tight seal with a convex end face of a cylindrical medicine syringe within the needleless injector.

5 Claims, 5 Drawing Figures

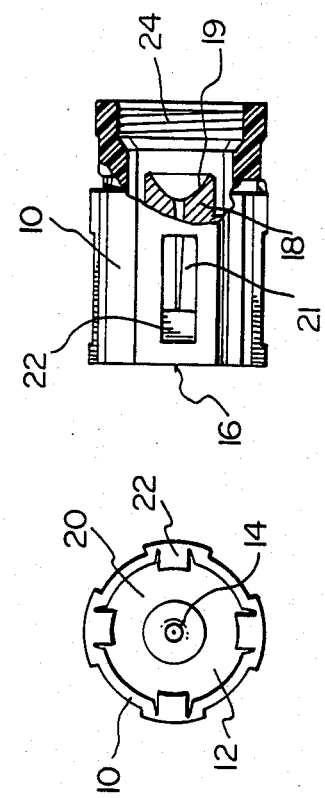
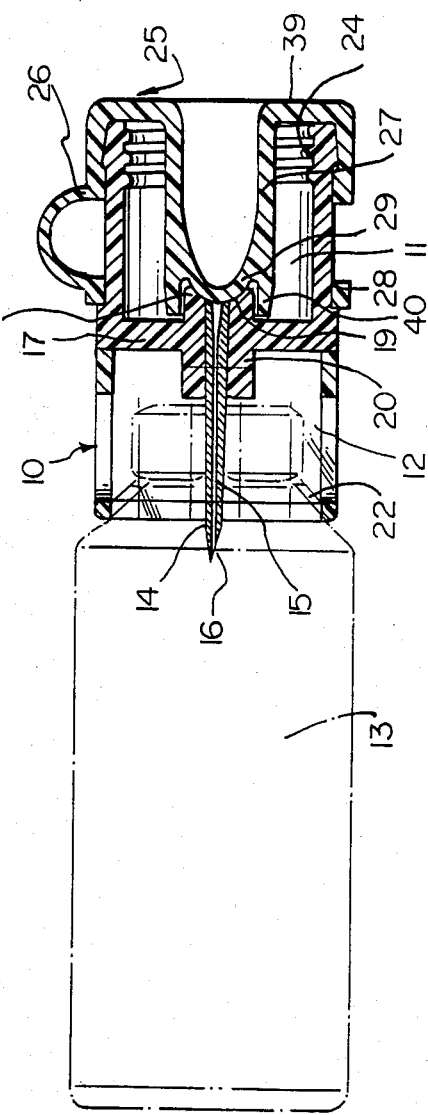
FIG. 1
FIG. 2
FIG. 3

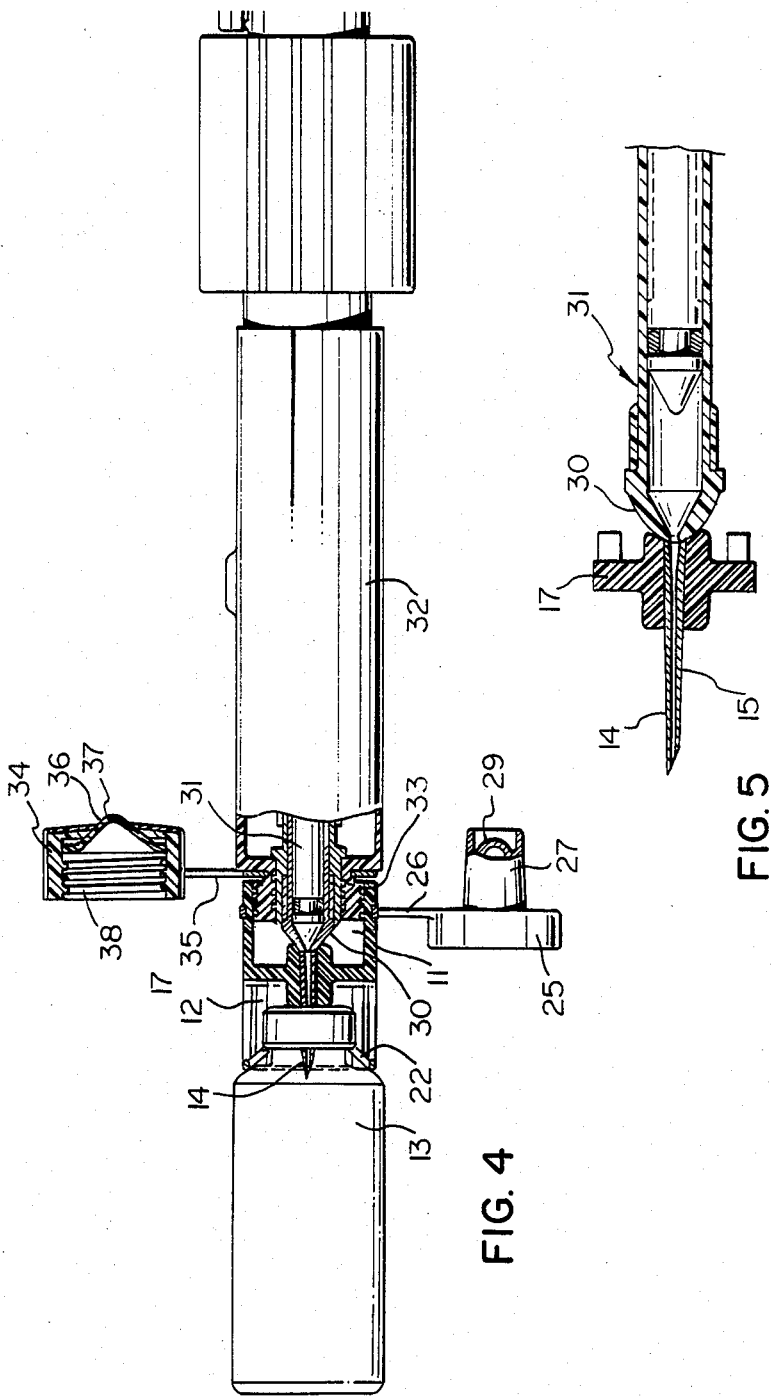

MEDICINE VIAL ADAPTOR FOR NEEDLELESS INJECTOR

BACKGROUND OF THE INVENTION

1. Field of the Invention

This invention relates to a disposable plastic adaptor for connecting a medicine vial to a needleless injector.

2. Discussion of the Prior Art

Recently there have been many improvements in needleless injectors for medicines. Improved designs include those shown in Lindmayer, et al., U.S. patent application Ser. No. 485,046, filed Apr. 14, 1983 and in Lindmayer, et al., U.S. Pat. No. 4,518,385 issued May 21, 1985.

A basic reason for the limited use of such injectors has been the difficulties and inconvenience involved in injecting different medicines using the same injector. Generally, it has been necessary to sterilize an injector used to inject one medicine before using the same injector for injecting another medicine. However, modern medicine relies to a great extent on sterile disposable products and needleless injectors must meet this requirement to achieve wide public acceptance.

U.S. Pat. No. 4,518,385 describes a disposable syringe for use in a needleless injector. As described in that patent, it is highly desirable to have the disposable syringe in a form which can be accurately filled to a required dosage rather than being pre-filled with a fixed amount of medicine. This, of course, necessitates a convenient means for transferring medicine from a standard medicine vial to the syringe. The above patent describes one such device which includes a hollow body portion for fitting over the end of a standard medicine vial and a needle for puncturing the top end of the medicine vial.

It is an object of the present invention to provide a simple disposable medicine vial adaptor which remains permanently fixed to the medicine vial and is simply thrown away with the empty vial.

SUMMARY OF THE INVENTION

The present invention relates to a disposable plastic adaptor for connecting a medicine vial to a needleless injector. It includes a hollow, generally cylindrical body member having a top end and a bottom end, with a wall dividing said hollow body into a generally cylindrical top end cavity and bottom end cavity. The bottom end cavity is adapted to slide over the top end of a medicine vial and the cavity wall includes a plurality of detents which prevent removal of the adaptor from the vial. The top end cavity is adapted to be twist connected to the end of a needleless injector. A fluid connector member is mounted within the body member and it comprises a sharp tipped probe extending axially downwardly within the bottom end cavity and an axial projection with a concave end face extending axially upwardly within the top end cavity. An axial bore extends through the fluid connector member to flow connect the concave end face and the probe tip. This probe, preferably in the form of a hollow needle, is adapted to penetrate the top of a medicine vial and the concave end face is adapted to provide a fluid tight seal with a convex end face of a cylindrical medicine syringe within the needleless injector.

The disposable adaptor of the invention is stored in a hermetically sealed, sterile plastic bag and, in use, is removed from the bag and pushed over the end of a medicine vial. The needle punctures the top of the vial providing access to the medicine therein and the detents snap over the end of the vial such that once the disposable adaptor has been placed on the top of the vial, it can no longer be removed. In this manner, the disposable adaptor can be used for removing all or only part of the medicine from the vial. If only part of the medicine is removed, a snug cap can be used for the top end of the adaptor to prevent any contamination and it can thereby continue to be used at different times until the vial is empty. The empty vial with the adaptor attached is then simply thrown away.

BRIEF DESCRIPTION OF THE DRAWINGS

The invention will now be described in greater detail wih reference to the accompanying drawings, which illustrate certain preferred embodiments of the invention. In the drawings:

FIG. 1 is a side elevation of the adaptor in partial section;

FIG. 2 is an end elevation of the adaptor of FIG. 1;

FIG. 3 is a side elevation and partial section showing the adaptor connected to a medicine vial;

FIG. 4 is a side elevation and partial section showing the adaptor and medicine vial connected to a needleless injector; and FIG. 5 is an enlarged sectional view of part of FIG. 4.

The adaptor has a plastic body 10 with a generally cylindrical cavity 11 at the top end and a further generally cylindrical cavity 12 at the bottom end. The top and bottom cavities may conveniently be separated by a divider wall 17.

The bottom cavity 12 is adapted to fit over the top of a standard medicine vial 13. The cavity includes adjacent the bottom edge thereof inwardly and upwardly inclined flexible teeth 22, these being formed by pressing portions of the body 10 inwardly, leaving holes 21. These teeth flex outwardly as the adaptor is pushed onto the end of the medicine vial 13 and, when the adaptor is in position, the teeth 22 snap back into the positions shown in FIG. 3 such that the adaptor cannot be removed from the vial 13.

Extending axially downwardly through the bottom cavity 12 is a needle 14 having an axial bore 15 extending therethrough and a sharpened tip 16. The needle 14 passes through the divider wall 17, as well as through an upper axial projection 18 and a lower axial projection 20 on the divider wall. The top end of the upper axial projection 18 has a concave face 19 and the upper end of the needle bore 15 flow connects to the center of the concave end face. The inner face of the top cavity 11 also includes a thread 24 for connecting the adaptor to a needleless injector. Although a threaded connection is shown, a bayonet connection may equally well be used. The top end of the cavity 11 is preferably protected by a snuggly fitting cap 25 which is connected to the adaptor by way of a flexible strap 26 and a ring 28. This cap includes an axial cylindrical projection 27 extending from end wall 39. The end of projection 27 remote from end wall 39 includes a central convex portion 29 which mates with the concave portion 19 of the fluid connector, thereby providing a tight seal for the central bore 15. The concave portion 19 is recessed within a cylindrical skirt 40, which protects the concave portion from contamination when the cap is not closing the end of the adaptor, and which fits around the axial projection 18 when the cap closes the end of the adaptor as shown in FIG. 3.

When the medicine vial 13 and adaptor 10 are to be connected to a needleless injector 32, the cover cap 25 is removed and is preferably held by strap 26 as shown in FIG. 4. The top end cavity 11 of the adaptor is then twist connected onto a threaded cylindrical projection 33 on the end of the needleless injector 32 with the tapered end 30 of a medicine syringe 31 within the needleless injector 32 being in fluid tight engagement with the concave surface 19. The end tip of tapered end 30 includes a central orifice to receive the medicine from the vial. The syringe 31 and injector 32 may conveniently be of the type shown in U.S. Pat. No. 4,518,385, incorporated herein by reference.

With the vial and adaptor connected as shown in FIGS. 3 and 4, the required amount of medicine is drawn from the vial through the bore 15 and through the aligned orifice in the tip 30 into syringe 31. Then, the adaptor is removed from the injector and injection head 34 (shown connected to the injector 32 by way of flexible strap 35) is twist connected to threaded projection 33 on the end of injector 32. The injection head 34 includes a cylindrical plastic casing holding a metallic insert 36 containing an injection orifice 37. It is attached to the injector by means of internal thread 38. With the injection head 34 attached, an injection is made in the manner described in U.S. Pat. No. 4,518,385 and U.S. application Ser. No. 485,046.

I claim:

1. A disposable plastic adaptor for connecting a medicine vial to a needleless injector comprising
   a hollow, generally cylindrical body member having a top end and a bottom end,
   a wall dividing said hollow body into a generally cylindrical top end cavity and bottom end cavity, said bottom end cavity being adapted to slide over the top end of a medicine vial, said cavity wall including a plurality of detents which prevent removal of the adaptor from the vial, and said top end cavity being adapted to be twist connected to the end of a needleless injector and a fluid connector member mounted within said body member comprising a sharp tipped, hollow probe extending axially downwardly within said bottom end cavity and an axial projection with a cancave end face extending axially upwardly within said top end cavity and an axial bore extending through said fluid connector member to flow connect said concave end face and the probe tip, said probe being adapted to penetrate the top of a medicine vial and said concave end face being adapted to provide a fluid tight seal with the convex end of a cylindrical medicine reservoir within said needleless injector, and
   a protective cap member for protecting said top end cavity when the adaptor is not connected to a needleless injector, said protective cap comprising an end portion adapted to snuggly close the top end of said adaptor and having an inner cylindrical projection extending axially from the end portion, said cylindrical projection having at the end thereof remote from said cap end portion a cylindrical skirt with a convex end face recessed within said skirt, said convex end face being adapted to provide a fluid tight seal with the concave end face of said top end cavity axial projection and said skirt being adapted to protect said convex end face, and flexible connector means for retaining the protective cap in association with the cylindrical body member.

2. A disposable adaptor according to claim 1 wherein said hollow probe is a hollow needle.

3. A disposable adaptor according to claim 1 wherein said top cavity is threaded to mate with a threaded projection on the needleless injector.

4. A disposable adaptor according to claim 1 wherein said top cavity has a bayonet connector to mate with bayonet connector on a projection on the needleless injector.

5. A disposable adaptor according to claim 1 wherein said detents are flexible teeth inclined inwardly and upwardly from the bottom end of the cavity wall.

* * * * *